(12) United States Patent
Spivey et al.

(10) Patent No.: US 8,480,689 B2
(45) Date of Patent: Jul. 9, 2013

(54) SUTURING DEVICE

(75) Inventors: James T. Spivey, Cincinnati, OH (US); Kempton K. Carroll, II, Cincinnati, OH (US); David B. Griffith, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 892 days.

(21) Appl. No.: 12/202,740

(22) Filed: Sep. 2, 2008

(65) Prior Publication Data

US 2010/0057108 A1    Mar. 4, 2010

(51) Int. Cl.
    *A61B 17/08*    (2006.01)
(52) U.S. Cl.
    USPC ............ 606/148; 606/144; 606/147; 606/222
(58) Field of Classification Search
    USPC .......................... 606/139, 144–148, 205–209
    See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

Michael S. Kavic, M.D., "Natural Orifice Translumenal Endoscopic Surgery: "Notes"", JSLS, vol. 10, pp. 133-134 (2006).

(Continued)

*Primary Examiner* — Corrine M McDermott
*Assistant Examiner* — Todd J Scherbel

(57) ABSTRACT

A surgical suturing device has a grasper device that is translatable within an outer lumen where a first end of a needle is grasped with the grasper device. The needle may be resilient to a curved resting state. The grasper device translates proximally relative to the outer lumen such that the needle is translated into the outer lumen, wherein the outer lumen tends to straighten the needle from the curved resting state. The grasper device may be translated distally relative to the outer lumen such that a second end of the needle extends distally from the outer lumen and pierces the tissue. The needle may return to the curved resting state as it exits the outer lumen. When a second end of the needle emerges from the tissue, the second end of the needle may be grasped with the grasper device.

5 Claims, 19 Drawing Sheets

U.S. PATENT DOCUMENTS

| | | | |
|---|---|---|---|
| 3,170,471 A | 2/1965 | Schnitzer | |
| 3,435,824 A | 4/1969 | Gamponia | |
| 3,470,876 A | 10/1969 | Barchilon | |
| 3,595,239 A | 7/1971 | Petersen | |
| 3,669,487 A | 6/1972 | Roberts et al. | |
| 3,746,881 A | 7/1973 | Fitch et al. | |
| 3,799,672 A | 3/1974 | Vurek | |
| 3,854,473 A | 12/1974 | Matsuo | |
| 3,946,740 A | 3/1976 | Bassett | |
| 3,948,251 A | 4/1976 | Hosono | |
| 3,994,301 A | 11/1976 | Agris | |
| 4,011,872 A | 3/1977 | Komiya | |
| 4,012,812 A | 3/1977 | Black | |
| 4,085,743 A * | 4/1978 | Yoon | 606/140 |
| 4,164,225 A | 8/1979 | Johnson et al. | |
| 4,178,920 A | 12/1979 | Cawood, Jr. et al. | |
| 4,207,873 A | 6/1980 | Kruy | |
| 4,235,238 A | 11/1980 | Ogiu et al. | |
| 4,258,716 A | 3/1981 | Sutherland | |
| 4,269,174 A | 5/1981 | Adair | |
| 4,278,077 A | 7/1981 | Mizumoto | |
| 4,285,344 A | 8/1981 | Marshall | |
| 4,311,143 A | 1/1982 | Komiya | |
| 4,329,980 A | 5/1982 | Terada | |
| 4,396,021 A | 8/1983 | Baumgartner | |
| 4,406,656 A | 9/1983 | Hattler et al. | |
| 4,452,246 A | 6/1984 | Bader et al. | |
| 4,461,281 A | 7/1984 | Carson | |
| 4,491,132 A | 1/1985 | Aikins | |
| 4,527,331 A | 7/1985 | Lasner et al. | |
| 4,527,564 A | 7/1985 | Eguchi et al. | |
| 4,538,594 A | 9/1985 | Boebel et al. | |
| D281,104 S | 10/1985 | Davison | |
| 4,569,347 A | 2/1986 | Frisbie | |
| 4,580,551 A | 4/1986 | Siegmund et al. | |
| 4,646,722 A | 3/1987 | Silverstein et al. | |
| 4,653,476 A | 3/1987 | Bonnet | |
| 4,655,219 A * | 4/1987 | Petruzzi | 606/206 |
| 4,669,470 A | 6/1987 | Brandfield | |
| 4,671,477 A | 6/1987 | Cullen | |
| 4,685,447 A | 8/1987 | Iversen et al. | |
| 4,711,240 A | 12/1987 | Goldwasser et al. | |
| 4,712,545 A | 12/1987 | Honkanen | |
| 4,721,116 A | 1/1988 | Schintgen et al. | |
| 4,733,662 A | 3/1988 | DeSatnick et al. | |
| D295,894 S | 5/1988 | Sharkany et al. | |
| 4,763,669 A | 8/1988 | Jaeger | |
| 4,770,188 A | 9/1988 | Chikama | |
| 4,815,450 A | 3/1989 | Patel | |
| 4,823,794 A | 4/1989 | Pierce | |
| 4,829,999 A | 5/1989 | Auth | |
| 4,867,140 A | 9/1989 | Hovis et al. | |
| 4,873,979 A | 10/1989 | Hanna | |
| 4,880,015 A | 11/1989 | Nierman | |
| 4,911,148 A | 3/1990 | Sosnowski et al. | |
| 4,926,860 A | 5/1990 | Stice et al. | |
| 4,938,214 A | 7/1990 | Specht et al. | |
| 4,950,273 A | 8/1990 | Briggs | |
| 4,950,285 A | 8/1990 | Wilk | |
| 4,960,133 A | 10/1990 | Hewson | |
| 4,977,887 A | 12/1990 | Gouda | |
| 4,979,950 A | 12/1990 | Transue et al. | |
| 4,984,581 A | 1/1991 | Stice | |
| 5,007,917 A | 4/1991 | Evans | |
| 5,010,876 A | 4/1991 | Henley et al. | |
| 5,020,514 A | 6/1991 | Heckele | |
| 5,020,535 A | 6/1991 | Parker et al. | |
| 5,025,778 A | 6/1991 | Silverstein et al. | |
| 5,033,169 A | 7/1991 | Bindon | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,050,585 A | 9/1991 | Takahashi | |
| 5,052,372 A | 10/1991 | Shapiro | |
| 5,065,516 A | 11/1991 | Dulebohn | |
| 5,066,295 A | 11/1991 | Kozak et al. | |
| 5,123,913 A | 6/1992 | Wilk et al. | |
| 5,123,914 A | 6/1992 | Cope | |
| 5,133,727 A | 7/1992 | Bales et al. | |
| 5,147,374 A | 9/1992 | Fernandez | |
| 5,174,300 A | 12/1992 | Bales et al. | |
| 5,176,126 A | 1/1993 | Chikama | |
| 5,190,050 A | 3/1993 | Nitzsche | |
| 5,190,555 A | 3/1993 | Wetter et al. | |
| 5,192,284 A | 3/1993 | Pleatman | |
| 5,201,752 A | 4/1993 | Brown et al. | |
| 5,201,908 A | 4/1993 | Jones | |
| 5,203,785 A | 4/1993 | Slater | |
| 5,203,787 A | 4/1993 | Noblitt et al. | |
| 5,209,747 A | 5/1993 | Knoepfler | |
| 5,217,003 A | 6/1993 | Wilk | |
| 5,217,453 A | 6/1993 | Wilk | |
| 5,219,357 A | 6/1993 | Honkanen et al. | |
| 5,219,358 A * | 6/1993 | Bendel et al. | 606/222 |
| 5,222,362 A | 6/1993 | Maus et al. | |
| 5,222,965 A | 6/1993 | Haughton | |
| 5,234,437 A | 8/1993 | Sepetka | |
| 5,234,453 A | 8/1993 | Smith et al. | |
| 5,235,964 A | 8/1993 | Abenaim | |
| 5,242,456 A | 9/1993 | Nash et al. | |
| 5,246,424 A | 9/1993 | Wilk | |
| 5,257,999 A * | 11/1993 | Slanetz, Jr. | 606/147 |
| 5,259,366 A | 11/1993 | Reydel et al. | |
| 5,263,958 A | 11/1993 | deGuillebon et al. | |
| 5,273,524 A | 12/1993 | Fox et al. | |
| 5,275,607 A | 1/1994 | Lo et al. | |
| 5,284,128 A | 2/1994 | Hart | |
| 5,284,162 A * | 2/1994 | Wilk | 128/898 |
| 5,287,845 A | 2/1994 | Faul et al. | |
| 5,290,299 A | 3/1994 | Fain et al. | |
| 5,290,302 A | 3/1994 | Pericic | |
| 5,295,977 A | 3/1994 | Cohen et al. | |
| 5,297,536 A | 3/1994 | Wilk | |
| 5,301,061 A | 4/1994 | Nakada et al. | |
| 5,312,333 A | 5/1994 | Churinetz et al. | |
| 5,312,351 A | 5/1994 | Gerrone | |
| 5,312,416 A | 5/1994 | Spaeth et al. | |
| 5,312,423 A | 5/1994 | Rosenbluth et al. | |
| 5,320,636 A | 6/1994 | Slater | |
| 5,325,845 A | 7/1994 | Adair | |
| 5,330,471 A | 7/1994 | Eggers | |
| 5,330,486 A | 7/1994 | Wilk | |
| 5,330,488 A | 7/1994 | Goldrath | |
| 5,330,496 A | 7/1994 | Alferness | |
| 5,330,502 A | 7/1994 | Hassler et al. | |
| 5,331,971 A | 7/1994 | Bales et al. | |
| 5,334,198 A | 8/1994 | Hart et al. | |
| 5,344,428 A | 9/1994 | Griffiths | |
| 5,350,391 A | 9/1994 | Iacovelli | |
| 5,352,184 A | 10/1994 | Goldberg et al. | |
| 5,352,222 A | 10/1994 | Rydell | |
| 5,354,302 A | 10/1994 | Ko | |
| 5,354,311 A | 10/1994 | Kambin et al. | |
| 5,356,408 A | 10/1994 | Rydell | |
| 5,364,408 A | 11/1994 | Gordon | |
| 5,364,410 A | 11/1994 | Failla et al. | |
| 5,366,466 A | 11/1994 | Christian et al. | |
| 5,366,467 A | 11/1994 | Lynch et al. | |
| 5,368,605 A | 11/1994 | Miller, Jr. | |
| 5,370,647 A | 12/1994 | Graber et al. | |
| 5,370,679 A | 12/1994 | Atlee, III | |
| 5,374,273 A | 12/1994 | Nakao et al. | |
| 5,374,275 A | 12/1994 | Bradley et al. | |
| 5,374,277 A | 12/1994 | Hassler | |
| 5,377,695 A | 1/1995 | An Haack | |
| 5,383,877 A | 1/1995 | Clarke | |
| 5,383,888 A | 1/1995 | Zvenyatsky et al. | |
| 5,386,817 A | 2/1995 | Jones | |
| 5,391,174 A * | 2/1995 | Weston | 606/148 |
| 5,392,789 A | 2/1995 | Slater et al. | |
| 5,395,386 A | 3/1995 | Slater | |
| 5,401,248 A | 3/1995 | Bencini | |
| 5,403,328 A | 4/1995 | Shallman | |
| 5,403,342 A | 4/1995 | Tovey et al. | |
| 5,403,348 A | 4/1995 | Bonutti | |
| 5,405,073 A | 4/1995 | Porter | |
| 5,405,359 A | 4/1995 | Pierce | |

| | | | | | | |
|---|---|---|---|---|---|---|
| 5,409,478 A | 4/1995 | Gerry et al. | | 5,669,875 A | 9/1997 | van Eerdenburg |
| 5,417,699 A | 5/1995 | Klein et al. | | 5,681,324 A | 10/1997 | Kammerer et al. |
| 5,423,821 A | 6/1995 | Pasque | | 5,681,330 A | 10/1997 | Hughett et al. |
| 5,433,721 A | 7/1995 | Hooven et al. | | 5,685,820 A | 11/1997 | Riek et al. |
| 5,439,471 A | 8/1995 | Kerr | | 5,690,656 A | 11/1997 | Cope et al. |
| 5,439,478 A | 8/1995 | Palmer | | 5,690,660 A | 11/1997 | Kauker et al. |
| 5,441,059 A | 8/1995 | Dannan | | 5,695,448 A | 12/1997 | Kimura et al. |
| 5,441,499 A | 8/1995 | Fritzsch | | 5,695,505 A | 12/1997 | Yoon |
| 5,443,463 A | 8/1995 | Stern et al. | | 5,695,511 A | 12/1997 | Cano et al. |
| 5,445,638 A | 8/1995 | Rydell et al. | | 5,700,275 A | 12/1997 | Bell et al. |
| 5,449,021 A | 9/1995 | Chikama | | 5,702,438 A | 12/1997 | Avitall |
| 5,456,667 A | 10/1995 | Ham et al. | | 5,704,892 A | 1/1998 | Adair |
| 5,456,684 A | 10/1995 | Schmidt et al. | | 5,709,708 A | 1/1998 | Thal |
| 5,458,131 A | 10/1995 | Wilk | | 5,716,326 A | 2/1998 | Dannan |
| 5,458,583 A | 10/1995 | McNeely et al. | | 5,730,740 A | 3/1998 | Wales et al. |
| 5,460,168 A | 10/1995 | Masubuchi et al. | | 5,735,849 A | 4/1998 | Baden et al. |
| 5,460,629 A | 10/1995 | Shlain et al. | | 5,741,234 A | 4/1998 | Aboul-Hosn |
| 5,462,561 A | 10/1995 | Voda | | 5,741,278 A | 4/1998 | Stevens |
| 5,465,731 A | 11/1995 | Bell et al. | | 5,741,285 A | 4/1998 | McBrayer et al. |
| 5,467,763 A | 11/1995 | McMahon et al. | | 5,746,759 A | 5/1998 | Meade et al. |
| 5,468,250 A | 11/1995 | Paraschac et al. | | 5,749,881 A | 5/1998 | Sackier et al. |
| 5,470,308 A | 11/1995 | Edwards et al. | | 5,749,889 A | 5/1998 | Bacich et al. |
| 5,470,320 A | 11/1995 | Tiefenbrun et al. | | 5,752,951 A | 5/1998 | Yanik |
| 5,478,347 A | 12/1995 | Aranyi | | 5,755,731 A | 5/1998 | Grinberg |
| 5,480,404 A | 1/1996 | Kammerer et al. | | 5,766,167 A | 6/1998 | Eggers et al. |
| 5,482,054 A | 1/1996 | Slater et al. | | 5,766,170 A | 6/1998 | Eggers |
| 5,484,451 A | 1/1996 | Akopov et al. | | 5,766,205 A | 6/1998 | Zvenyatsky et al. |
| 5,489,256 A | 2/1996 | Adair | | 5,769,849 A | 6/1998 | Eggers |
| 5,496,347 A | 3/1996 | Hashiguchi et al. | | 5,779,701 A | 7/1998 | McBrayer et al. |
| 5,499,990 A | 3/1996 | Schülken et al. | | 5,779,716 A | 7/1998 | Cano et al. |
| 5,499,992 A | 3/1996 | Meade et al. | | 5,779,727 A | 7/1998 | Orejola |
| 5,501,692 A | 3/1996 | Riza | | 5,782,859 A | 7/1998 | Nicholas et al. |
| 5,503,616 A | 4/1996 | Jones | | 5,782,866 A | 7/1998 | Wenstrom, Jr. |
| 5,505,686 A | 4/1996 | Willis et al. | | 5,791,022 A | 8/1998 | Bohman |
| 5,507,755 A | 4/1996 | Gresl et al. | | 5,792,113 A | 8/1998 | Kramer et al. |
| 5,511,564 A | 4/1996 | Wilk | | 5,792,153 A | 8/1998 | Swain et al. |
| 5,514,157 A | 5/1996 | Nicholas et al. | | 5,792,165 A | 8/1998 | Klieman et al. |
| 5,522,829 A | 6/1996 | Michalos | | 5,797,835 A | 8/1998 | Green |
| 5,522,830 A | 6/1996 | Aranyi | | 5,797,928 A | 8/1998 | Kogasaka |
| 5,527,321 A | 6/1996 | Hinchliffe | | 5,797,939 A | 8/1998 | Yoon |
| 5,536,248 A | 7/1996 | Weaver et al. | | 5,797,941 A | 8/1998 | Schulze et al. |
| 5,540,648 A | 7/1996 | Yoon | | 5,803,903 A | 9/1998 | Athas et al. |
| 5,554,151 A | 9/1996 | Hinchliffe | | 5,808,665 A | 9/1998 | Green |
| 5,555,883 A | 9/1996 | Avitall | | 5,810,806 A | 9/1998 | Ritchart et al. |
| 5,558,133 A | 9/1996 | Bortoli et al. | | 5,810,849 A | 9/1998 | Kontos |
| 5,562,693 A | 10/1996 | Devlin et al. | | 5,810,865 A | 9/1998 | Koscher et al. |
| 5,569,243 A | 10/1996 | Kortenbach et al. | | 5,810,876 A | 9/1998 | Kelleher |
| 5,569,298 A | 10/1996 | Schnell | | 5,810,877 A | 9/1998 | Roth et al. |
| 5,573,540 A | 11/1996 | Yoon | | 5,813,976 A | 9/1998 | Filipi et al. |
| 5,578,030 A | 11/1996 | Levin | | 5,814,058 A | 9/1998 | Carlson et al. |
| 5,582,611 A | 12/1996 | Tsuruta et al. | | 5,817,061 A | 10/1998 | Goodwin et al. |
| 5,582,617 A | 12/1996 | Klieman et al. | | 5,817,107 A | 10/1998 | Schaller |
| 5,584,845 A | 12/1996 | Hart | | 5,817,119 A | 10/1998 | Klieman et al. |
| 5,591,179 A | 1/1997 | Edelstein | | 5,819,736 A | 10/1998 | Avny et al. |
| 5,593,420 A | 1/1997 | Eubanks, Jr et al. | | 5,827,281 A | 10/1998 | Levin |
| 5,595,562 A | 1/1997 | Grier | | 5,827,299 A | 10/1998 | Thomason et al. |
| 5,597,378 A | 1/1997 | Jervis | | 5,830,231 A | 11/1998 | Geiges, Jr. |
| 5,601,573 A | 2/1997 | Fogelberg et al. | | 5,833,700 A | 11/1998 | Fogelberg et al. |
| 5,601,588 A | 2/1997 | Tonomura et al. | | 5,833,703 A | 11/1998 | Manushakian |
| 5,604,531 A | 2/1997 | Iddan et al. | | 5,843,017 A | 12/1998 | Yoon |
| 5,607,389 A | 3/1997 | Edwards et al. | | 5,843,121 A * | 12/1998 | Yoon .......................... 606/206 |
| 5,607,450 A | 3/1997 | Zvenyatsky et al. | | 5,849,022 A | 12/1998 | Sakashita et al. |
| 5,613,975 A | 3/1997 | Christy | | 5,853,374 A | 12/1998 | Hart et al. |
| 5,618,303 A | 4/1997 | Marlow et al. | | 5,855,585 A | 1/1999 | Kontos |
| 5,620,415 A | 4/1997 | Lucey et al. | | 5,860,913 A | 1/1999 | Yamaya et al. |
| 5,624,399 A | 4/1997 | Ackerman | | 5,860,995 A | 1/1999 | Berkelaar |
| 5,624,431 A | 4/1997 | Gerry et al. | | 5,868,762 A | 2/1999 | Cragg et al. |
| 5,626,578 A | 5/1997 | Tihon | | 5,876,411 A | 3/1999 | Kontos |
| 5,628,732 A | 5/1997 | Antoon, Jr. et al. | | 5,882,331 A | 3/1999 | Sasaki |
| 5,630,782 A | 5/1997 | Adair | | 5,882,344 A | 3/1999 | Stouder, Jr. |
| 5,643,283 A | 7/1997 | Younker | | 5,893,846 A | 4/1999 | Bales et al. |
| 5,643,292 A | 7/1997 | Hart | | 5,893,874 A | 4/1999 | Bourque et al. |
| 5,643,294 A | 7/1997 | Tovey et al. | | 5,893,875 A | 4/1999 | O'Connor et al. |
| 5,644,798 A | 7/1997 | Shah | | 5,899,919 A | 5/1999 | Eubanks, Jr. et al. |
| 5,645,083 A | 7/1997 | Essig et al. | | 5,902,254 A | 5/1999 | Magram |
| 5,649,372 A | 7/1997 | Souza | | 5,904,702 A | 5/1999 | Ek et al. |
| 5,653,677 A | 8/1997 | Okada et al. | | 5,908,420 A | 6/1999 | Parins et al. |
| 5,653,722 A | 8/1997 | Kieturakis | | 5,911,737 A | 6/1999 | Lee et al. |
| 5,662,663 A | 9/1997 | Shallman | | 5,916,147 A | 6/1999 | Boury |

| | | | |
|---|---|---|---|
| 5,921,993 A * | 7/1999 | Yoon ............................. 606/140 |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,549 A | 9/1999 | Richardson et al. |
| 5,954,720 A | 9/1999 | Wilson et al. |
| 5,954,731 A | 9/1999 | Yoon |
| 5,957,943 A | 9/1999 | Vaitekunas |
| 5,957,953 A | 9/1999 | DiPoto et al. |
| 5,971,995 A | 10/1999 | Rousseau |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A * | 11/1999 | Yoon ............................. 606/170 |
| 5,989,182 A | 11/1999 | Hori et al. |
| 5,993,447 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,634 A | 2/2000 | Wu et al. |
| 6,033,399 A | 3/2000 | Gines |
| 6,036,685 A | 3/2000 | Mueller |
| 6,053,927 A | 4/2000 | Hamas |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A * | 6/2000 | Freeman ....................... 606/205 |
| 6,086,530 A | 7/2000 | Mack |
| 6,090,108 A | 7/2000 | McBrayer et al. |
| 6,096,046 A | 8/2000 | Weiss |
| 6,102,926 A | 8/2000 | Tartaglia et al. |
| 6,106,473 A | 8/2000 | Violante et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,159,200 A | 12/2000 | Verdura et al. |
| 6,165,184 A | 12/2000 | Verdura et al. |
| 6,168,570 B1 | 1/2001 | Ferrera |
| 6,168,605 B1 | 1/2001 | Measamer et al. |
| 6,170,130 B1 | 1/2001 | Hamilton et al. |
| 6,179,776 B1 | 1/2001 | Adams et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,214,007 B1 | 4/2001 | Anderson |
| 6,228,096 B1 | 5/2001 | Marchand |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,322,578 B1 | 11/2001 | Houle et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,035 B1 | 3/2002 | Manushakian |
| 6,361,534 B1 | 3/2002 | Chen et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,391,029 B1 | 5/2002 | Hooven et al. |
| 6,402,735 B1 | 6/2002 | Langevin |
| 6,406,440 B1 | 6/2002 | Stefanchik |
| 6,409,733 B1 | 6/2002 | Conlon et al. |
| 6,427,089 B1 | 7/2002 | Knowlton |
| 6,431,500 B1 | 8/2002 | Jacobs et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,520,954 B2 | 2/2003 | Ouchi |
| 6,543,456 B2 | 4/2003 | Freeman |
| 6,551,270 B1 | 4/2003 | Bimbo et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,585,642 B2 | 7/2003 | Christopher |
| 6,585,717 B1 | 7/2003 | Wittenberger et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 * | 8/2003 | Christy et al. ................. 606/148 |
| 6,610,074 B2 | 8/2003 | Santilli |
| 6,620,193 B1 | 9/2003 | Lau et al. |
| 6,626,919 B1 | 9/2003 | Swanstrom |
| 6,632,229 B1 | 10/2003 | Yamanouchi |
| 6,638,286 B1 | 10/2003 | Burbank et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |

| Patent | Date | Inventor |
|---|---|---|
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francese et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,255,675 B2 | 8/2007 | Gertner et al. |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |

| Patent | Date | Name |
|---|---|---|
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,222 B2 | 7/2008 | Asakura |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,674,259 B2 | 3/2010 | Shadduck |
| 7,713,189 B2 | 5/2010 | Hanke |
| 7,713,270 B2 * | 5/2010 | Suzuki ............................ 606/46 |
| 7,736,374 B2 | 6/2010 | Vaughan et al. |
| 7,744,615 B2 | 6/2010 | Couture |
| 7,758,577 B2 | 7/2010 | Nobis et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,780,691 B2 | 8/2010 | Stefanchik |
| 7,794,409 B2 | 9/2010 | Damarati |
| 7,794,475 B2 | 9/2010 | Hess et al. |
| 7,828,186 B2 | 11/2010 | Wales |
| 7,837,615 B2 | 11/2010 | Le et al. |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,887 B2 | 3/2011 | Rimbaugh et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,931,624 B2 | 4/2011 | Smith et al. |
| 7,945,332 B2 | 5/2011 | Schechter |
| 7,947,000 B2 | 5/2011 | Vargas et al. |
| 7,955,298 B2 | 6/2011 | Carroll et al. |
| 7,963,975 B2 | 6/2011 | Criscuolo |
| 7,988,685 B2 | 8/2011 | Ziaie et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0004515 A1 | 1/2005 | Hart et al. |
| 2005/0033265 A1 | 2/2005 | Engel et al. |
| 2005/0033277 A1 | 2/2005 | Clague et al. |

| | | |
|---|---|---|
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1* | 4/2005 | Sancoff et al. .................. 606/148 |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247576 A1 | 11/2006 | Poncet |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |

| | | |
|---|---|---|
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1* | 7/2009 | Surti et al. .................. 600/106 |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1* | 12/2009 | Stefanchik et al. .......... 606/144 |

| | | | | | | |
|---|---|---|---|---|---|---|
| 2009/0299406 A1 | 12/2009 | Swain et al. | EP | 0818974 B1 | 7/2001 | |
| 2009/0299409 A1 | 12/2009 | Coe et al. | EP | 1281356 A2 | 2/2003 | |
| 2009/0306658 A1 | 12/2009 | Nobis et al. | EP | 0947166 B1 | 5/2003 | |
| 2009/0306683 A1 | 12/2009 | Zwolinski et al. | EP | 0836832 B1 | 12/2003 | |
| 2009/0322864 A1 | 12/2009 | Karasawa et al. | EP | 1402837 A1 | 3/2004 | |
| 2009/0326561 A1 | 12/2009 | Carroll, II et al. | EP | 0744918 B1 | 4/2004 | |
| 2010/0010294 A1 | 1/2010 | Conlon et al. | EP | 0931515 B1 | 8/2004 | |
| 2010/0010298 A1 | 1/2010 | Bakos et al. | EP | 0941128 B1 | 10/2004 | |
| 2010/0010299 A1 | 1/2010 | Bakos et al. | EP | 1411843 B1 | 10/2004 | |
| 2010/0010303 A1 | 1/2010 | Bakos | EP | 1150614 B1 | 11/2004 | |
| 2010/0010510 A1 | 1/2010 | Stefanchik | EP | 1477104 A1 | 11/2004 | |
| 2010/0010511 A1 | 1/2010 | Harris et al. | EP | 1481642 A1 | 12/2004 | |
| 2010/0023032 A1 | 1/2010 | Granja Filho | EP | 1493391 A1 | 1/2005 | |
| 2010/0036198 A1 | 2/2010 | Tacchino et al. | EP | 0848598 B1 | 2/2005 | |
| 2010/0042045 A1 | 2/2010 | Splvey | EP | 1281360 B1 | 3/2005 | |
| 2010/0048990 A1 | 2/2010 | Bakos | EP | 1568330 A1 | 8/2005 | |
| 2010/0049190 A1 | 2/2010 | Long et al. | EP | 1452143 B1 | 9/2005 | |
| 2010/0049223 A1 | 2/2010 | Granja Filho | EP | 1616527 A2 | 1/2006 | |
| 2010/0056861 A1 | 3/2010 | Spivey | EP | 1006888 B1 | 3/2006 | |
| 2010/0056862 A1 | 3/2010 | Bakos | EP | 1629764 A1 | 3/2006 | |
| 2010/0057085 A1 | 3/2010 | Holcomb et al. | EP | 1013229 B1 | 6/2006 | |
| 2010/0063538 A1 | 3/2010 | Spivey et al. | EP | 1721561 A1 | 11/2006 | |
| 2010/0076451 A1 | 3/2010 | Zwolinski et al. | EP | 1153578 B1 | 3/2007 | |
| 2010/0081877 A1 | 4/2010 | Vakharia | EP | 1334696 B1 | 3/2007 | |
| 2010/0087813 A1 | 4/2010 | Long | EP | 1769766 A1 | 4/2007 | |
| 2010/0113872 A1 | 5/2010 | Asada et al. | EP | 1836971 A2 | 9/2007 | |
| 2010/0121362 A1 | 5/2010 | Clague et al. | EP | 1836980 A1 | 9/2007 | |
| 2010/0130817 A1 | 5/2010 | Conlon | EP | 1854421 A2 | 11/2007 | |
| 2010/0130975 A1 | 5/2010 | Long | EP | 1857061 A1 | 11/2007 | |
| 2010/0131005 A1 | 5/2010 | Conlon | EP | 1875876 A1 | 1/2008 | |
| 2010/0152539 A1 | 6/2010 | Ghabrial et al. | EP | 1891881 A1 | 2/2008 | |
| 2010/0152609 A1 | 6/2010 | Zwolinski et al. | EP | 1902663 A1 | 3/2008 | |
| 2010/0152746 A1 | 6/2010 | Ceniccola et al. | EP | 1477106 B1 | 6/2008 | |
| 2010/0179510 A1 | 7/2010 | Fox et al. | EP | 1949844 A1 | 7/2008 | |
| 2010/0179530 A1 | 7/2010 | Long et al. | EP | 1518499 B1 | 8/2008 | |
| 2010/0191050 A1 | 7/2010 | Zwolinski | EP | 1709918 B1 | 10/2008 | |
| 2010/0191267 A1 | 7/2010 | Fox | EP | 1985226 A2 | 10/2008 | |
| 2010/0198005 A1 | 8/2010 | Fox | EP | 1994904 A1 | 11/2008 | |
| 2010/0198149 A1 | 8/2010 | Fox | EP | 1707130 B1 | 12/2008 | |
| 2010/0198244 A1 | 8/2010 | Spivey et al. | EP | 0723462 B1 | 3/2009 | |
| 2010/0198248 A1 | 8/2010 | Vakharia | EP | 1769749 B1 | 11/2009 | |
| 2010/0249700 A1 | 9/2010 | Spivey | EP | 1493397 B1 | 9/2011 | |
| 2010/0286791 A1 | 11/2010 | Goldsmith | FR | 2731610 A1 | 9/1996 | |
| 2010/0298642 A1 | 11/2010 | Trusty et al. | GB | 330629 A | 6/1930 | |
| 2010/0312056 A1 | 12/2010 | Galperin et al. | GB | 2335860 A | 10/1999 | |
| 2010/0331622 A2 | 12/2010 | Conlon | GB | 2403909 A | 1/2005 | |
| 2010/0331774 A2 | 12/2010 | Spivey | GB | 2421190 A | 6/2006 | |
| 2011/0093009 A1 | 4/2011 | Fox | GB | 2443261 A | 4/2008 | |
| 2011/0098694 A1 | 4/2011 | Long | JP | 56-46674 | 4/1981 | |
| 2011/0098704 A1 | 4/2011 | Long et al. | JP | 63309252 A | 12/1988 | |
| 2011/0105850 A1 | 5/2011 | Voegele et al. | JP | 4038960 A | 2/1992 | |
| 2011/0112434 A1 | 5/2011 | Ghabrial et al. | JP | 8-29699 A | 2/1996 | |
| 2011/0115891 A1 | 5/2011 | Trusty | JP | 2002-369591 A | 12/2002 | |
| 2011/0124964 A1 | 5/2011 | Nobis | JP | 2003-088494 A | 3/2003 | |
| 2011/0152609 A1 | 6/2011 | Trusty et al. | JP | 2003-235852 A | 8/2003 | |
| 2011/0152610 A1 | 6/2011 | Trusty et al. | JP | 2004-33525 A | 2/2004 | |
| 2011/0152612 A1 | 6/2011 | Trusty et al. | JP | 2004-065745 A | 3/2004 | |
| 2011/0152858 A1 | 6/2011 | Long et al. | JP | 2005-121947 A | 5/2005 | |
| 2011/0152859 A1 | 6/2011 | Long et al. | JP | 2005-261514 A | 9/2005 | |
| 2011/0152878 A1 | 6/2011 | Trusty et al. | JP | 2006297005 A | 11/2006 | |
| 2011/0152923 A1 | 6/2011 | Fox | NL | 1021295 C2 | 2/2004 | |
| 2011/0160514 A1 | 6/2011 | Long et al. | SU | 194230 | 5/1967 | |
| 2011/0190659 A1 | 8/2011 | Long et al. | SU | 980703 | 12/1982 | |
| 2011/0190764 A1 | 8/2011 | Long et al. | WO | WO 84/01707 A1 | 5/1984 | |
| 2011/0245619 A1 | 10/2011 | Holcomb | WO | WO 92/13494 A1 | 8/1992 | |
| 2011/0306971 A1 | 12/2011 | Long | WO | WO 93/10850 A1 | 6/1993 | |
| | | | WO | WO 93/20760 A1 | 10/1993 | |
| | FOREIGN PATENT DOCUMENTS | | WO | WO 93/20765 A1 | 10/1993 | |
| DE | 4323585 A1 | 1/1995 | WO | WO 95/09666 A1 | 4/1995 | |
| DE | 19713797 A1 | 10/1997 | WO | WO 96/22056 A1 | 7/1996 | |
| DE | 19757056 B4 | 8/2008 | WO | WO 96/27331 A1 | 9/1996 | |
| DE | 102006027873 B4 | 10/2009 | WO | WO 96/39946 A1 | 12/1996 | |
| EP | 0086338 A1 | 8/1983 | WO | WO 97/12557 A1 | 4/1997 | |
| EP | 0286415 A2 | 10/1988 | WO | WO 98/01080 A1 | 1/1998 | |
| EP | 0589454 A2 | 3/1994 | WO | WO 99/00060 A1 | 1/1999 | |
| EP | 0464479 B1 | 3/1995 | WO | WO 99/09919 A1 | 3/1999 | |
| EP | 0529675 B1 | 2/1996 | WO | WO 99/17661 A1 | 4/1999 | |
| EP | 0724863 B1 | 7/1999 | WO | WO 99/30622 A2 | 6/1999 | |
| EP | 0760629 B1 | 11/1999 | WO | WO 00/35358 A1 | 6/2000 | |

| | | | |
|---|---|---|---|
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A1 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (Notes)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey Notes Presentation to EES Notes Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Feb. 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-74.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis col. Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview &navRelId=1000.1003&method=D . . . , accessed Jul. 18, 2008 (4 pages).
U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 11/756,914, filed Jun. 1, 2007.
International Search Report for PCT/US2009/055008, Jan. 19, 2010 (9 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).

D. Wilhelm et al., "An Innovative, Safe and Sterile Sigmoid Access (ISSA) for Notes," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented at DDW Demonstrate Potential of Pure Notes Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal Notes Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal Notes Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.

U.S. Appl. No. 12/617,998, filed Nov. 13, 2009.
U.S. Appl. No. 12/635,298, filed Dec. 10, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
Written Opinion for PCT/US2009/055008, Jan. 19, 2010 (8 pages).
Zadno et al., "Linear Superelasticity in Cold-Worked Ni-Ti," Engineering Aspects of Shape Memory Alloys, pp. 414-419 (1990).
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./viewphp3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.

* cited by examiner

SUTURING DEVICE

BACKGROUND

Various embodiments are directed to surgical devices and methods of using the same.

In endoscopic, laparoscopic, and other noninvasive surgical techniques, internal suturing or other tissue fastening must be performed with instruments small enough to fit through a trocar or endoscope working channel, which can often be quite narrow. For example, the working channel of a typical flexible endoscope has a diameter in the range of about 2.5 to about 4 millimeters. Current staplers and suturing devices cannot be easily redesigned to work through such small openings. In addition, performing procedures by way of the working channel does not easily permit using two instruments positioned at different angles with respect to the wound site in order to "pass and catch" a needle and apply sutures.

Various clips, suture fasteners and anchors have been developed such that clinicians may endoscopically close tissue perforations resulting from, for example, ulcers, polypectomy, incisions, etc. One type of suture anchor is known as a "T-tag" fastener. The T-tag is a small metallic pin with a suture attached at the middle. The physician may load the T-tag into the end of a cannulated needle of an applicator that may be inserted through the working channel of an endoscope. The physician may push the needle into the tissue near the perforation and implant the T-tag into the tissue with the attached suture trailing through the working channel and out the proximal end of the endoscope. After two or more T-tags are attached to the tissue near the wound in this manner, the physician may pull the sutures to appose the tissue around the wound. The physician may then fasten the sutures together by applying a plurality of alternating, right and left overhand knots using a knot pushing device or by applying a knotting element or other type of fastener through the working channel of the endoscope.

FIGURES

The novel features of the various embodiments are set forth with particularity in the appended claims. The various embodiments, however, both as to organization and methods of operation, together with advantages thereof, may best be understood by reference to the following description, taken in conjunction with the accompanying drawings as follows.

DESCRIPTION

Various embodiments are directed to curved, flexible suturing needles as well as devices and methods for manipulating such needles to place sutures during surgical operations. A flexible needle may be made from any resilient, flexible material. In its rest position, the flexible needle may have a curved shape. In use, the needle may be provided to a surgical site through a hollow lumen, such as the working channel of an endoscope, a trocar, an accessory channel, etc. When the flexible needle is within the lumen, it may be held in a straight position. At the surgical site, the flexible needle may be extended through a distally facing end of the lumen where it may encounter and pierce tissue. As the needle exits the lumen and extends through the tissue, it may regain its curved shape. This may cause the needle to curve back on itself and exit the tissue, for example, through the same surface that it entered. A collet, jaws, or other grasper device may then be used to grasp the leading end of the needle, pull the needle through the tissue, and complete the stitch. For subsequent stitches, the needle may be retracted into the lumen to straighten it and then used again, for example, in the manner described above.

Figure 1:
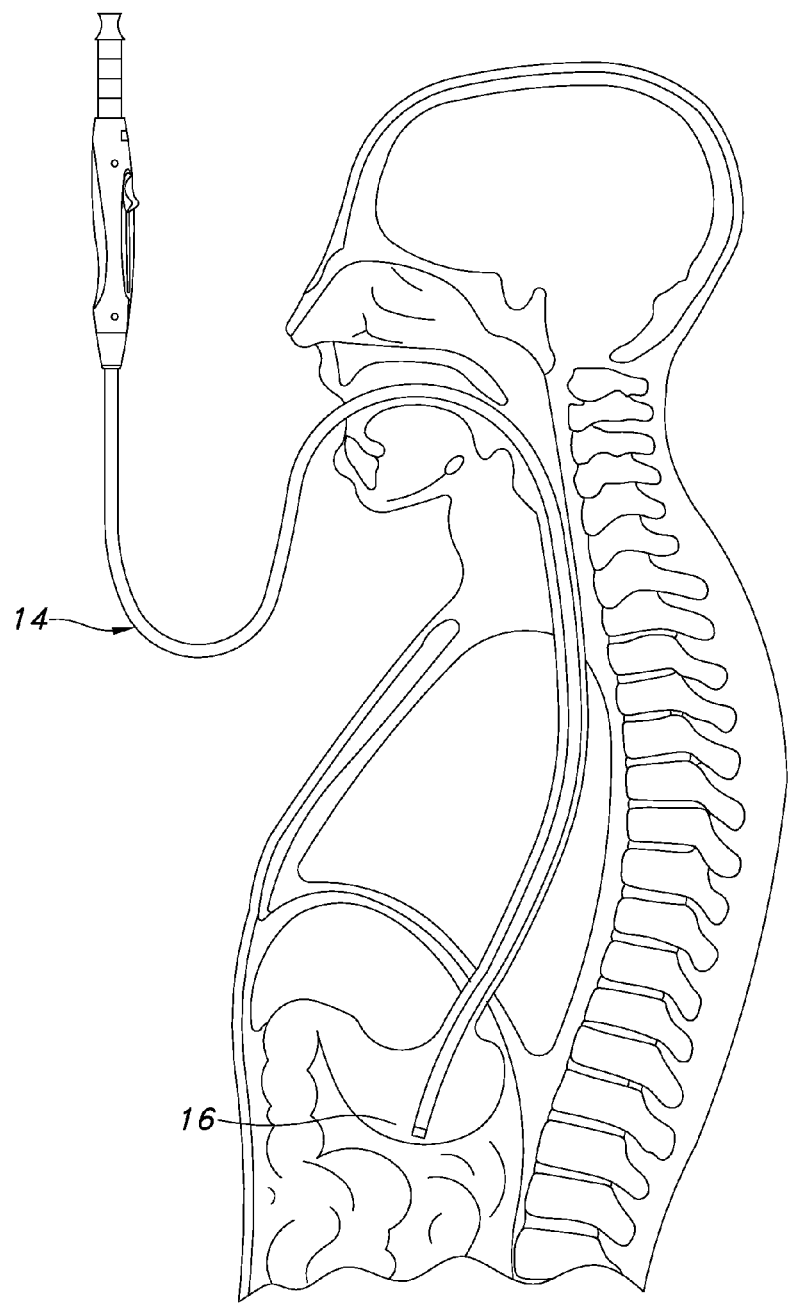
FIG. 1 is a drawing of one embodiment of an endoscope inserted into the upper gastrointestinal tract of a patient.

FIG. 1 illustrates one embodiment of an endoscope 14 (illustrated here as a gastroscope) inserted into the upper gastrointestinal tract of a patient. The endoscope 14 may be used to provide flexible suturing needles, and tools for manipulating the needles, to a surgical site, for example, as described herein. The endoscope 14 has a distal end 16 that may include various optical channels, illumination channels, and working channels. According to various embodiments, the endoscope 14 may be a flexible endoscope and may be introduced via natural orifices and may be combined with trans-organ techniques. In one embodiment, Natural Orifice Translumenal Endoscopic Surgery (NOTES)™ techniques may be employed to introduce instruments into the patient and carry out the various procedures described hereinbelow. A NOTES™ technique is a minimally invasive therapeutic procedure that may be employed to treat diseased tissue or perform other therapeutic operations through a natural opening of the patient without making incisions in the abdomen. A natural opening may be the mouth, anus, and/or vagina. Medical implantable instruments may be introduced into the patient to the target area via the natural opening. In a NOTES™ technique, a clinician inserts a flexible endoscope into one or more natural openings of the patient to view the target area using a camera. During endoscopic surgery, the clinician inserts surgical devices through one or more lumens or working channels of the endoscope 14 to perform various key surgical activities (KSA). These KSAs include forming an anastomosis between organs, repairing ulcers and other wounds, etc. In some embodiments, surgical devices may be provided to surgical sites other than through the working channel of an endoscope including, for example, via one or more accessory channels. Also, although the devices and methods described herein may be used with NOTES™ techniques, it will be appreciated that they may also be used with other surgical techniques including, for example, other endoscopic techniques, laparoscopic techniques, etc.

Figure 2:
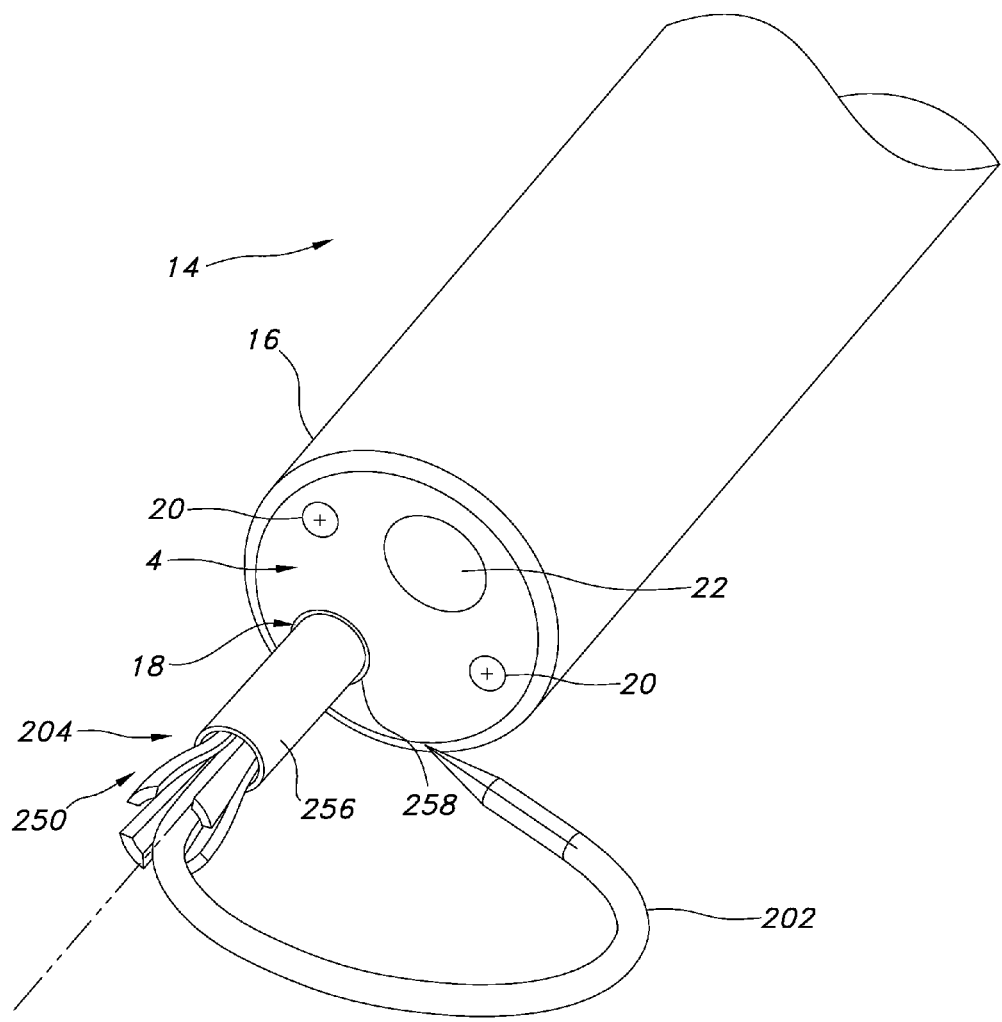
FIG. 2 illustrates one embodiment of a distal end of the endoscope of FIG. 1 showing a flexible needle and grasper device extending from a working channel.

FIG. 2 illustrates one embodiment of the distal end 16 of the endoscope 14 showing a flexible needle 202 and grasper device 204 extending from a working channel 18. The distal end 16 of the endoscope 14 comprises a distal face 4 defining illumination channels 20, an optical channel 22, and the working channel 18. The illumination channels 20 may comprise one or more optical fibers or other suitable waveguides for directing light from a proximally positioned light source (not shown) to the surgical site. The optical channel 22 may comprise one or more optical fibers or other suitable waveguides for receiving and transmitting an image of the surgical site proximally to a position where the image may be viewed by a clinician operating the endoscope 16. As described above, the working channel 10 may allow the clinician to introduce one or more surgical tools to the surgical site including, for example, the needle 202 and grasper device 204. It will be appreciated that the endoscope 14 as illustrated is but one example of an endoscope that may be used in accordance with various embodiments. Endoscopes having alternate configurations of optical channels 22, illumination channels 20 and/or working channels 18 may also be used.

Figure 3:
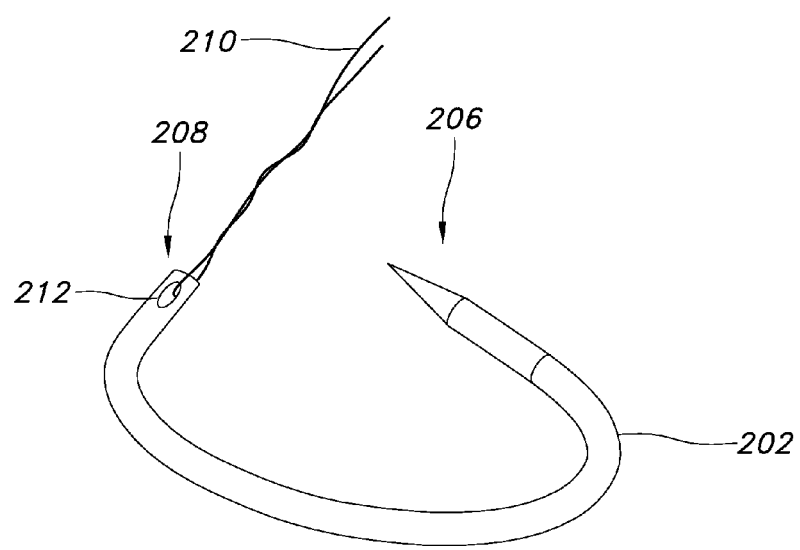
FIG. 3 illustrates one embodiment of the curved needle of FIG. 2.

FIG. 3 illustrates one embodiment of the curved needle 202. The needle 202 may comprise a sharp leading end 206 for piercing tissue and a back end 208. The back end 208 may define a suture hole 212, through which suture 210 may be threaded. According to various embodiments, the suture hole 212 may be placed at other positions in the needle 202 including, for example, at about a midpoint between the leading end 206 and the back end 208. The needle 202 may be made from any suitably resilient material. For example, the needle 202 may be made from nitinal (an alloy of Ni and Ti) or another shape memory alloy. In some embodiments, the needle 202 may be made from a resilient alloy of stainless steel or a suitable synthetic material. The resiliency of the needle 202 may allow it to return to the curved, rest position shown in FIG. 3 after it has been straightened, for example, to pass through the working channel 18 as described herein.

Figure 4A:
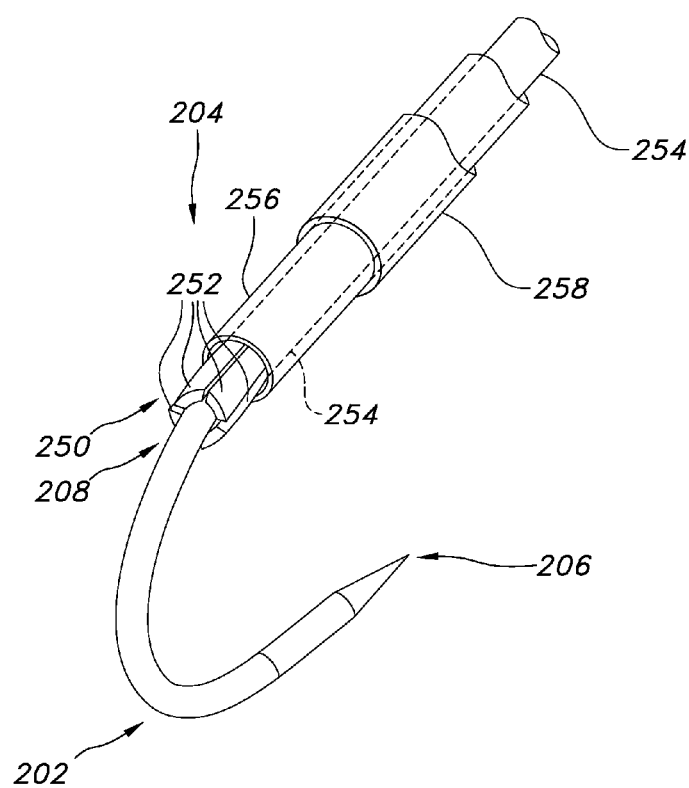
FIG. 4A illustrates one embodiment of the grasper device of FIG. 2 grasping the back end of the needle of FIGS. 2 and 3.

FIG. 4A illustrates one embodiment of the grasper device 204 grasping the back end 208 of the needle 202. Some components of the grasper device 204 are also illustrated in FIG. 2. The grasper device 204 may comprise a collet 250 positioned within a collet lumen 256. On its distal-facing end, the collet 250 may comprise a plurality of fingers 252. The proximal portions of the fingers 252 may merge into a flexible, collet shaft 254 that may extend proximally through the collet lumen 256. When the collet 250 is extended distally relative to the collet lumen 256, such that the fingers 252 clear the collet lumen 256, the fingers 252 may be separated from one another such that there is an opening between them. When the collet 250 is retracted proximally relative to the collet lumen 256, the collet lumen 256 may exert a force on the collet 250, causing the fingers 252 to close. In this way, the collet 250 may be used as a grasper to grasp the needle 202.

Figure 4B:
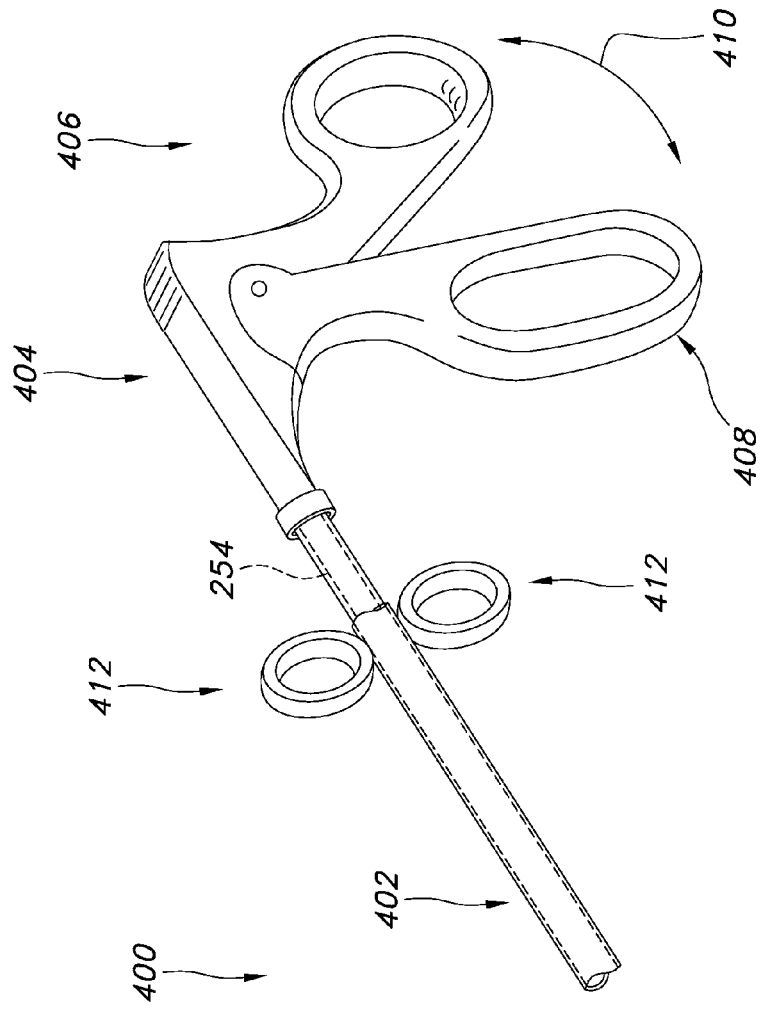
FIG. 4B illustrates one embodiment of a surgical instrument comprising the grasper device of FIG. 2, a shaft assembly and a handle or hand piece.

The collet 250 and collet lumen 256 may be actuated by the clinician to open and close the fingers 252 according to any suitable manner. For example, FIG. 4B illustrates one embodiment of a surgical instrument 400 comprising the grasper device 204, a shaft assembly 402 and a handle or hand piece 404. The hand piece 404 may be configured to be grasped by the clinician. In at least one embodiment, the hand piece 404 may comprise a pistol grip including a stationary member 406 and movable member, or trigger 408. In use, the trigger 408 may be moved toward the stationary member 406 as indicated by arrow 410, for example, in order to operate the grasper device 204 within a surgical site. The collet shaft 254 may extend proximally from the collet fingers 252 to the trigger 408. When the trigger 408 is moved toward the stationary member 406, it may cause a distally directed force to be exerted on the collet shaft 254. This may force the collet 250 in a distal direction relative to the collet lumen 256, causing the collet fingers 252 to open. The clinician may close the collet fingers 252 by moving the trigger 408 away from the stationary member 406. This may tend to pull the collet shaft 254 in a proximal direction relative to the collet lumen 256, which may pull the collet 250 into the collet lumen 256, causing the fingers 252 to close.

The grasper device 204 (e.g., the collet 250 and the collet lumen 256) may be slidably coupled within an outer lumen 258. Referring to FIG. 4B, the clinician may be able to slide the outer lumen 258 relative to the working channel 18 of the endoscope 14 and relative to grasper device 204. For example, near the position of the handle 404, the outer lumen 258 may be coupled to pair of loops 412 or other suitable control mechanism. The clinician may grasp the loops 412 and the handle 404 to change the relative positions of the outer lumen 258 and the grasper device 204. The clinician may also use the loops 412 to change the relative position of the outer lumen 258 and the working channel 18 of the endoscope 14 (not shown in FIG. 4B). In use, when the needle 202 is grasped by the grasper device 204, the grasper device 204 and the needle 202 may be retracted proximally relative to the outer lumen 258. This may bring the needle 202 within the walls of the outer lumen 258, which may force the needle 202 from its curved, rest position into a straight position. In some example embodiments, the outer lumen 258 may be omitted. For example, the walls of the working channel 18 may serve to straighten the needle 202. Also, for example, an accessory channel provided outside of the working channel 18 may be used to serve the function of the outer lumen 258.

Figure 5A:
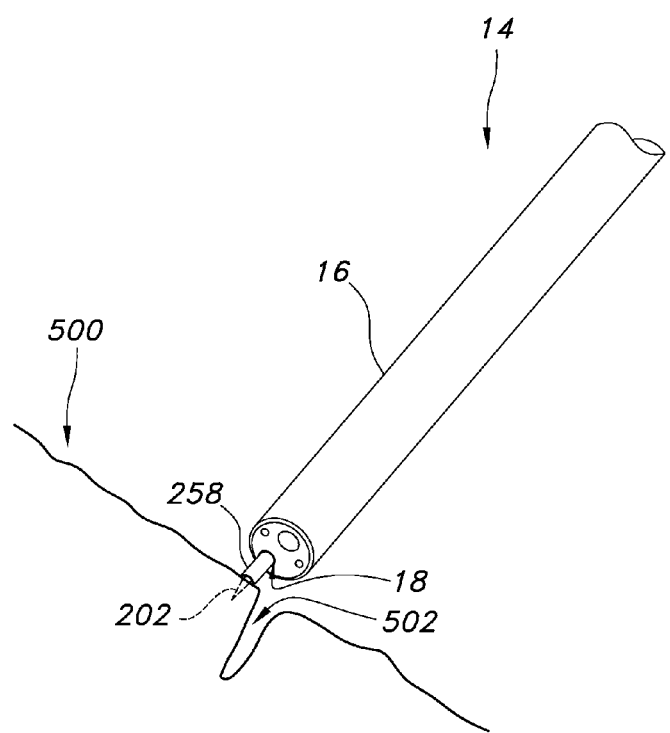
FIGS. 5A-5F illustrate one embodiment of a process for placing a stitch using the needle and grasper device of FIG. 2.

FIGS. 5A-5F illustrate one embodiment of a process for placing a stitch using the needle 202 and grasper device 204 described above. FIG. 5A illustrates one embodiment of the distal end 16 of the endoscope 14 in proximity to tissue 500 having a wound 502 to be sutured. The wound 502 may be, for example, an ulcer, incision or any other opening to be closed. The outer lumen 258 may be extended distally from the working channel 18 to be near or in contact with the tissue 500. Although the grasper device 204 is not visible in FIG. 5A, it may be positioned within the outer lumen 258. Also, for example, the needle 202 may be secured in the grasper device 204. The walls of the outer lumen 258 may hold the needle 202 in a straight position. When the outer lumen 258 is in position, as shown in FIG. 5A, the clinician may extend the needle 202 into the tissue 500, as shown, by extending the grasper device 204 distally relative to the outer lumen 258.

Figure 5B:
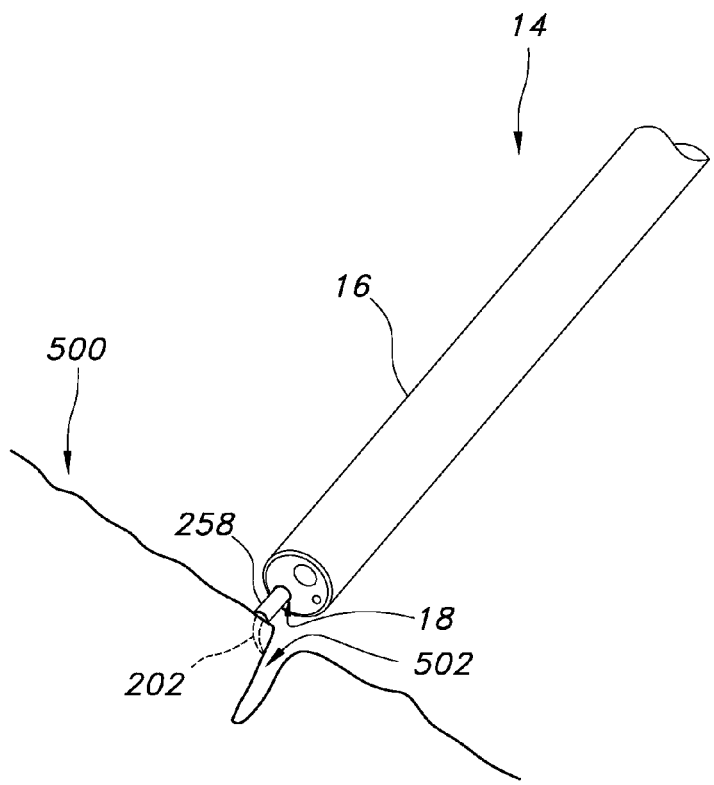
Figure 5C:
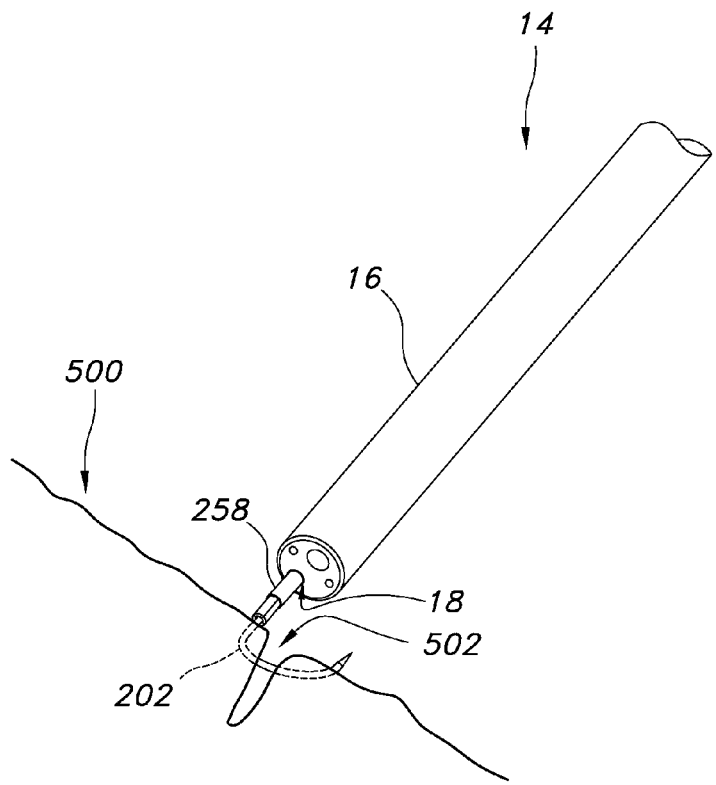

FIGS. 5B and 5C illustrate one embodiment of the needle 202 being pushed through the tissue 500. For example, the clinician may continue to extend the grasper device 204, and therefore the needle 202, distally within the outer lumen 258. As the needle 202 exits the outer lumen 258 and enters the tissue 500, it may tend to bend into its resting, curved shape, as shown. As more of the needle 202 enters the tissue, the curvature may increase, until the needle 202 bends back on itself and begins to exit the tissue 500, as shown in FIG. 5C.

Figure 5D:
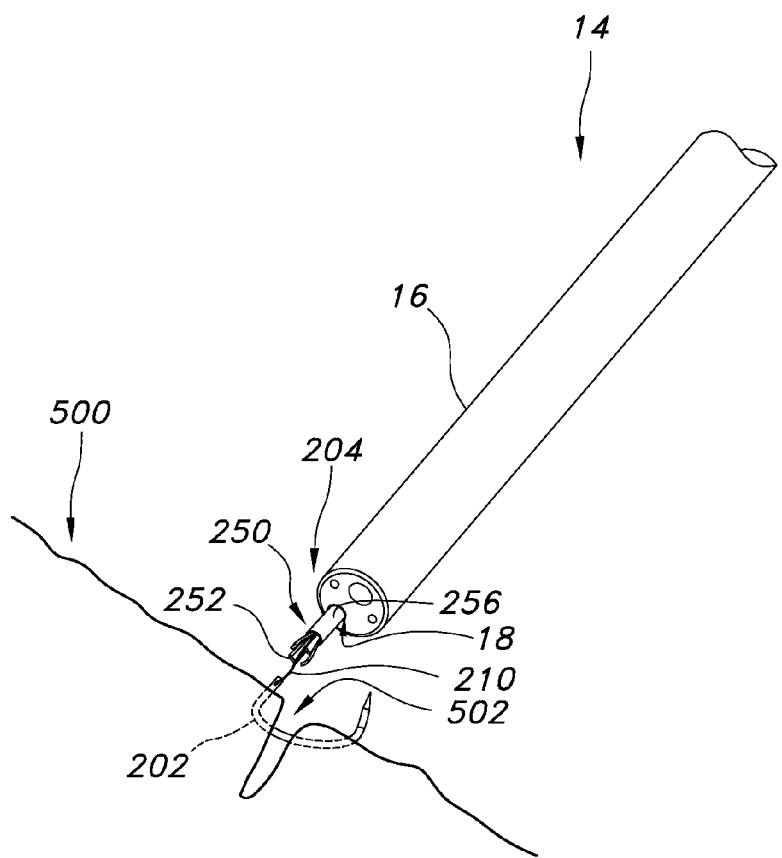

FIG. 5D illustrates one embodiment of the needle 202 after it has been released by the grasper device 204. When the needle 202 is fully extended into the tissue 500, the grasper device 204 may extend distally from the lumen 258 as shown. The clinician may then cause the grasper device 204 to release the needle 202. For example, the collet 250 may be extended distally relative to the collet lumen 256 (not shown in FIG. 5D) causing the fingers 252 to release, thus releasing the grip on the needle 202. The needle 202 may remain embedded in the tissue 500 as shown. The suture 210, as shown in FIG. 5D, may extend proximally, for example, through the working channel 18. According to various embodiments, the collet 250 may have a hollow center allowing, the suture 210 to extend proximally through the collet 250.

Figure 5E:
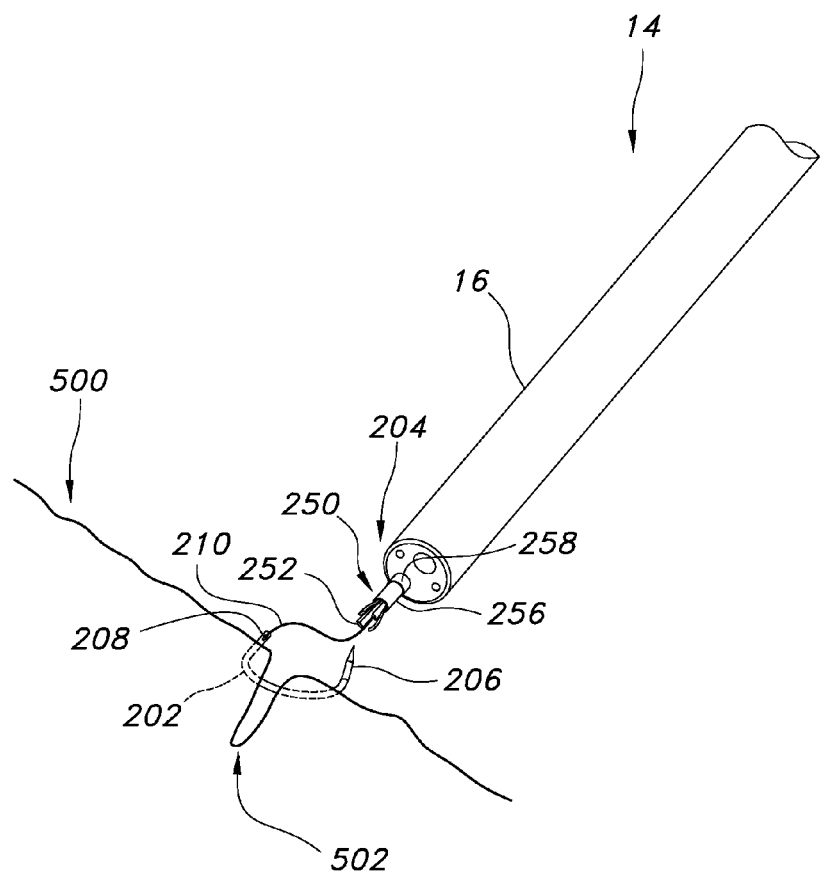
Figure 5F:
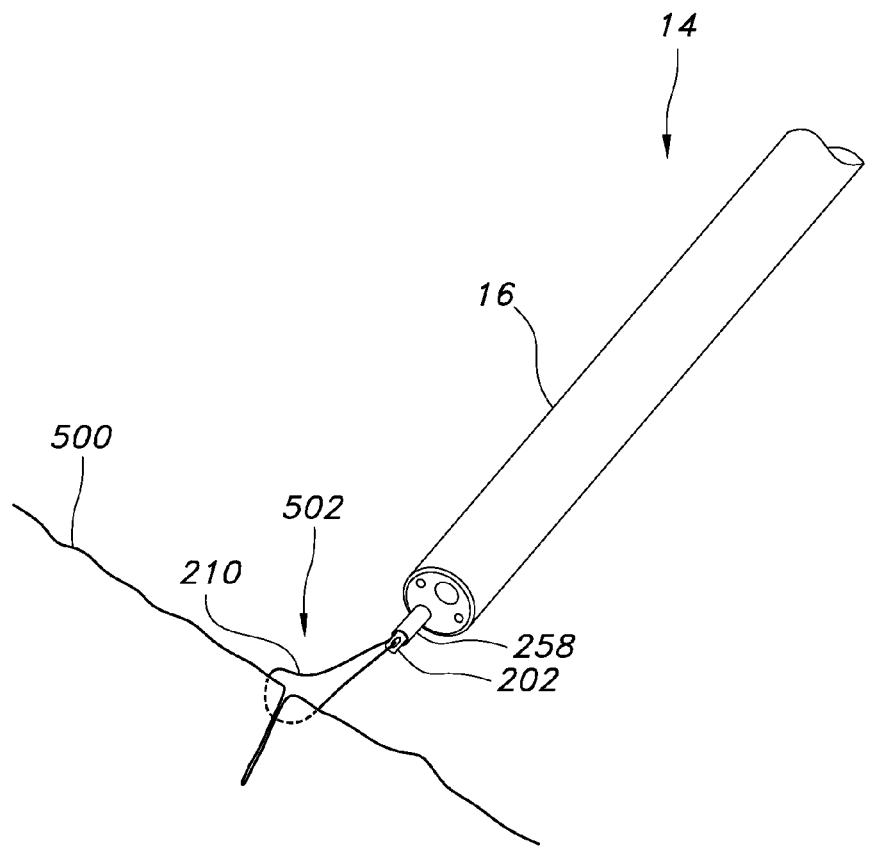

After the needle 202 is released, the clinician may cause the grasper device 204 to grasp the leading end 206 of the needle 202, as shown in FIG. 5E. The grasper device 204 may then be retracted proximally relative to the outer lumen 258. This may cause the needle 202 to be pulled proximally out of the tissue 500 and into the outer lumen 258. Accordingly, the suture 210 may form a stitch tending to close the wound 502. FIG. 5F illustrates one embodiment where the needle 202 is retracted into the outer lumen 258 as described. To begin a new stitch, the needle 202 may be pulled proximally out of the working channel 18. The needle 202 may then be reloaded into the working channel 18 or other access device (e.g., trocar, accessory channel, etc.) with the leading edge 206 facing distally. At that point, a new stitch may be placed, for example, as illustrated in FIGS. 5A-5F.

Figure 6:
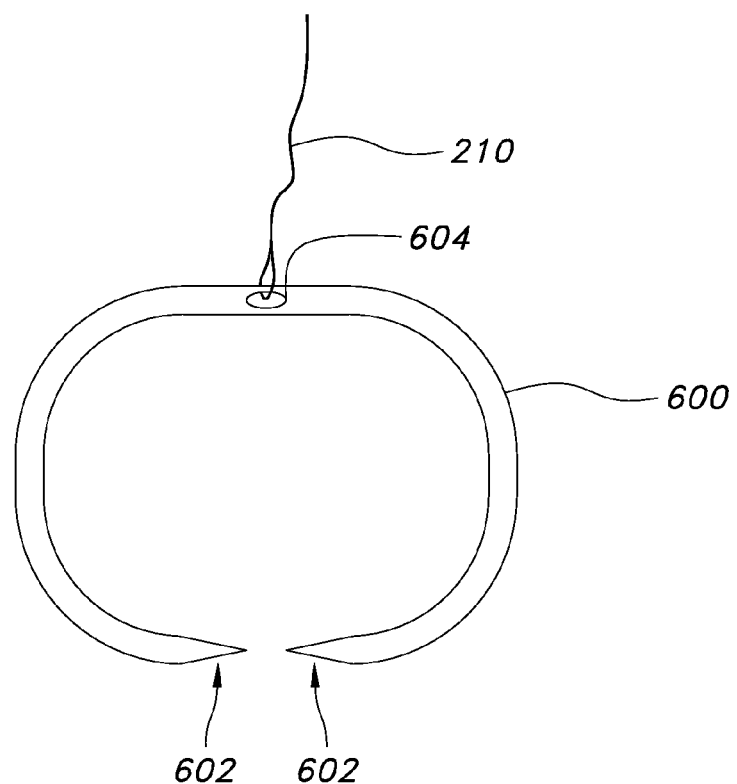
FIG. 6 illustrates one embodiment of a double-pointed needle that may be used with the grasper device of FIG. 2 to place a stitch.

FIG. 6 illustrates one embodiment of a double-pointed needle 600 that may be used with the grasper device 204 to place a stitch, for example, as described herein. The needle 600 may comprise two leading ends 602, each defining a point for piercing tissue. A suture hole 604 threaded with suture 210 is shown at approximately the mid-point of the needle 600. It will be appreciated, however, that the suture hole 604 may be positioned at any point in the needle 600. The needle 600 may be used to place a stitch in a manner similar to that described above with respect to FIGS. 5A-5F. It may not be necessary, however, to retract the needle 600 from the proximal end of the endoscope 14 after every stitch to turn it around. Because the needle 600 comprises two leading ends 602, it may always have one leading end 602 facing distally when it is in within the lumen 258. Accordingly, after being removed from the tissue 500 in a manner similar to that shown in FIG. 5F, the needle 600 may be retracted into the lumen 258 far enough to allow the lumen 258 to straighten the needle 600. Then the needle 600 may be used to place another stitch, this time with the opposite leading end 602 entering the tissue 500 first.

Figure 7:
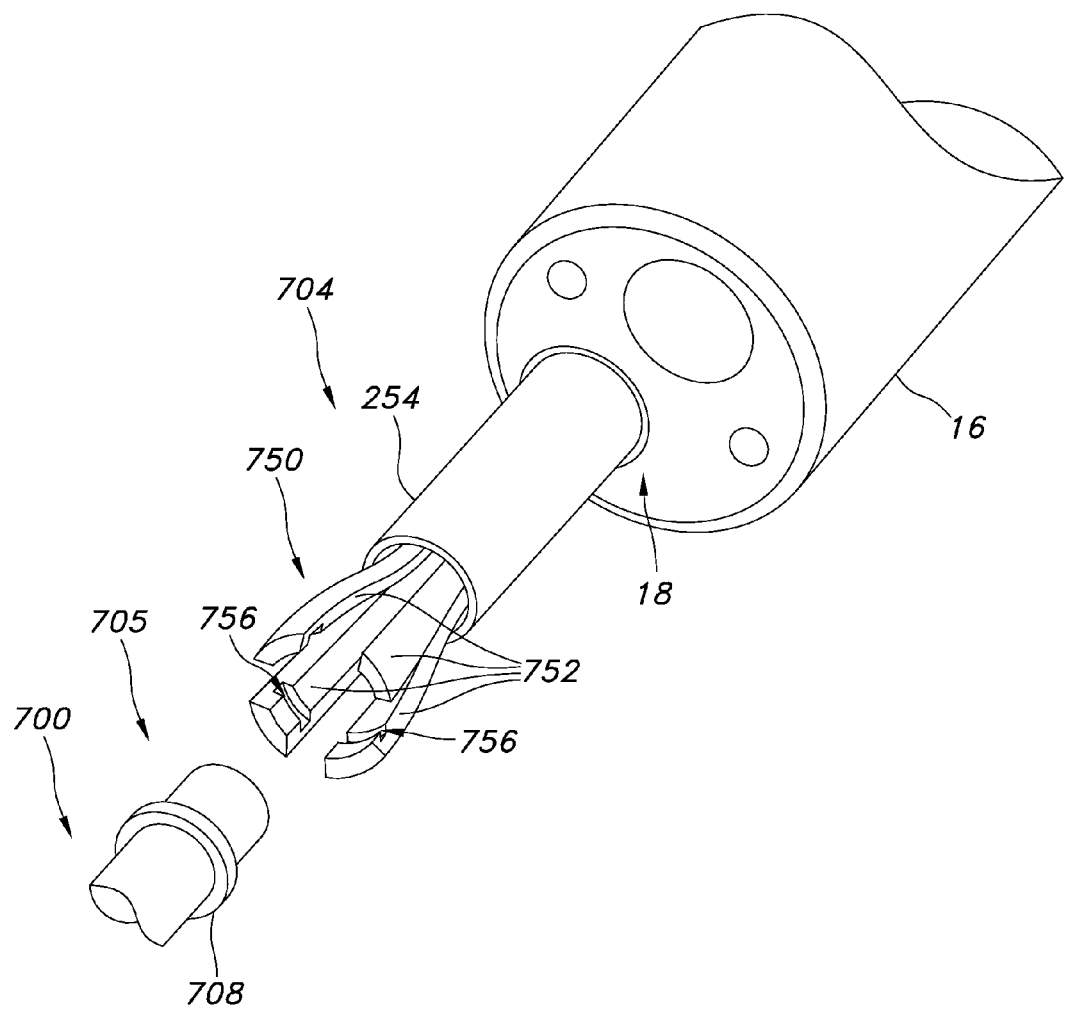
FIG. 7 illustrates one embodiment of a grasper device and a portion of a needle having corresponding gripping features.
Figure 8:
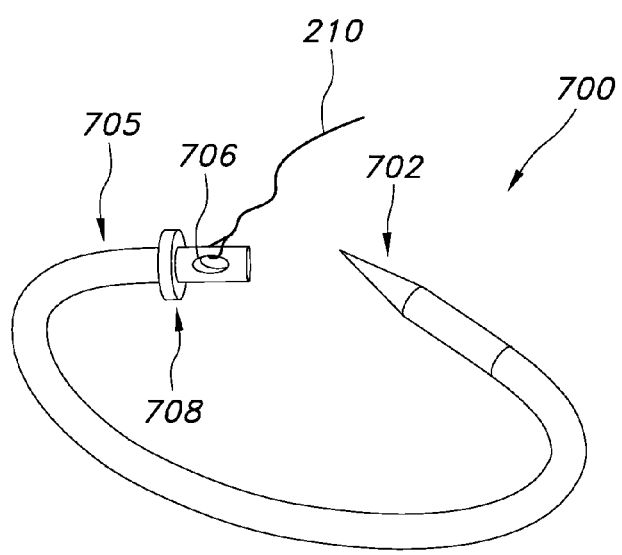
FIG. 8 is a full view of one embodiment of the needle shown in FIG. 7.

FIG. 7 illustrates one embodiment of a grasper device 704 and a portion of a needle 700 having corresponding gripping features. FIG. 8 is a full view of one embodiment of the needle 700. The needle 700 may have a leading end 702 and a back end 705. A suture hole 706 may be optionally placed at the back end 705, as shown in FIG. 8. Also at the back end 705, the needle 700 may have a collar 708 extending around the needle shaft. The grasper device 704 may have corresponding grooves 756, formed as a concave feature, in the fingers 752 of its collet 750. Accordingly, when the grasper device 704 grips the back end 705 of the needle 700, the grooves 756 may receive the collar 708. In this way, the grasper device 704 may obtain an improved grip on the needle 700 during the stitching process. In addition to, or instead of, the collar 708, the needle 700 and/or fingers 752 may include other gripping features including, for example, textured, friction-enhancing surfaces, or features having various other shapes.

Figure 9:
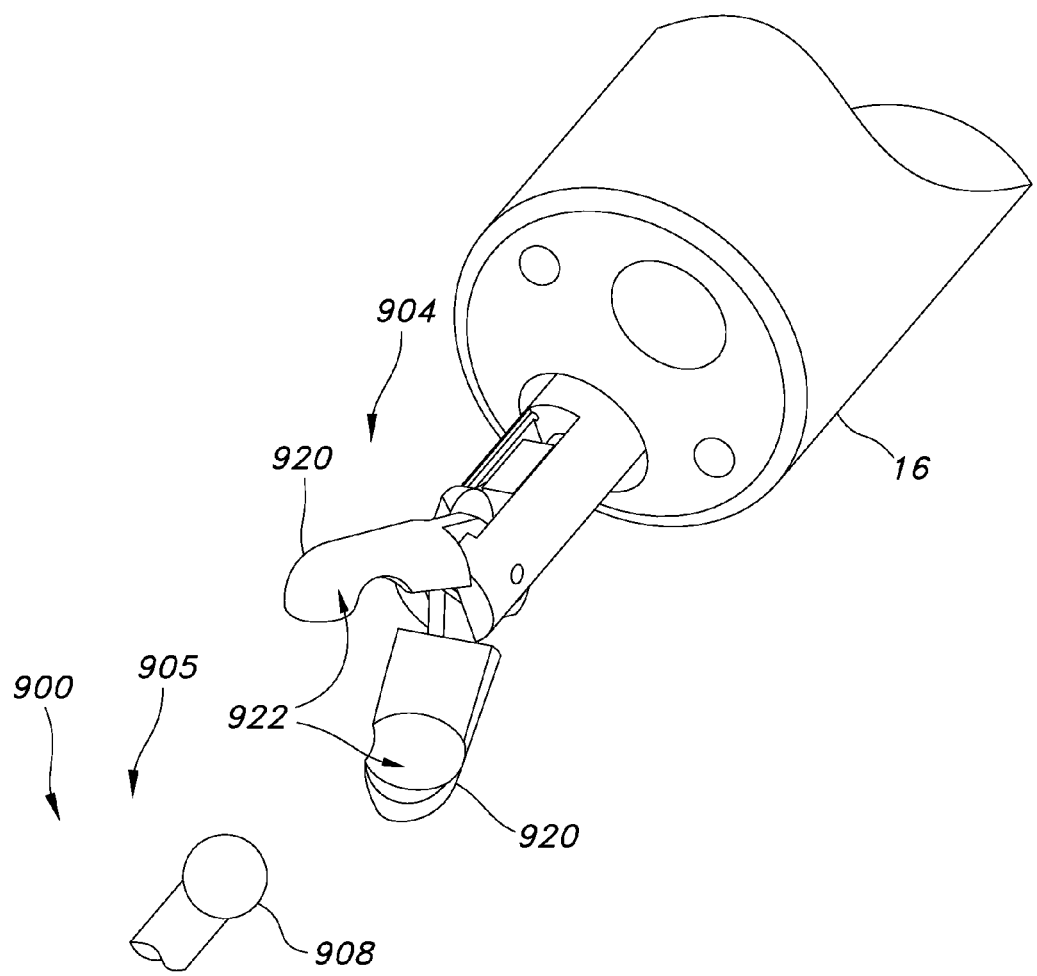
FIGS. 9 and 10 illustrate another embodiment of a needle and grasper device having gripping features.
Figure 10:
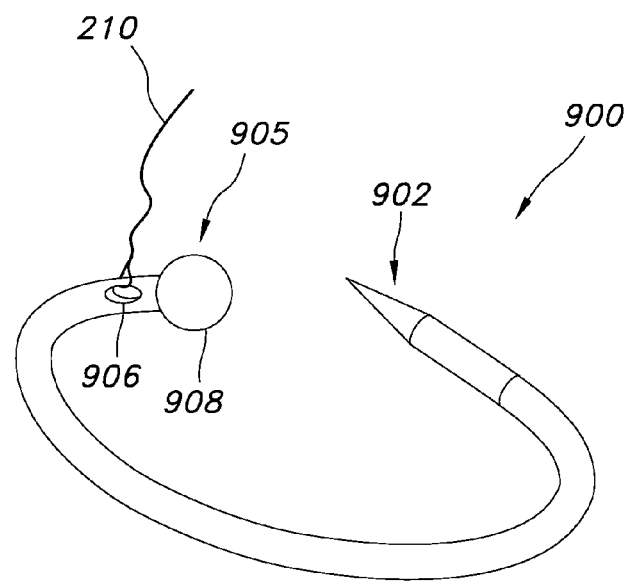

FIGS. 9 and 10 illustrate a needle 900 and grasper device 904 with another embodiment of a gripping feature. The needle 900 may have a leading end 902 and a back end 905. A suture hole 906 may be positioned at the back end 905 as shown, or at any other location on the needle 900. The needle 900 may also have a rounded or ball shaped feature 908 at its back end 905. The grasper device 904 may have a pair of jaw members 920 defining concave openings 922 configured to receive the ball 908. When the needle 900 is grasped by the jaw members 920, the ball 908 and cavities 922 may tend to improve the grip of the jaws 920 on the ball 908. Also, because of the round shape of the ball 908, the needle 900 may be free to pivot relative to the jaws 920 even when the jaws 920 are in a closed position.

Figure 11:
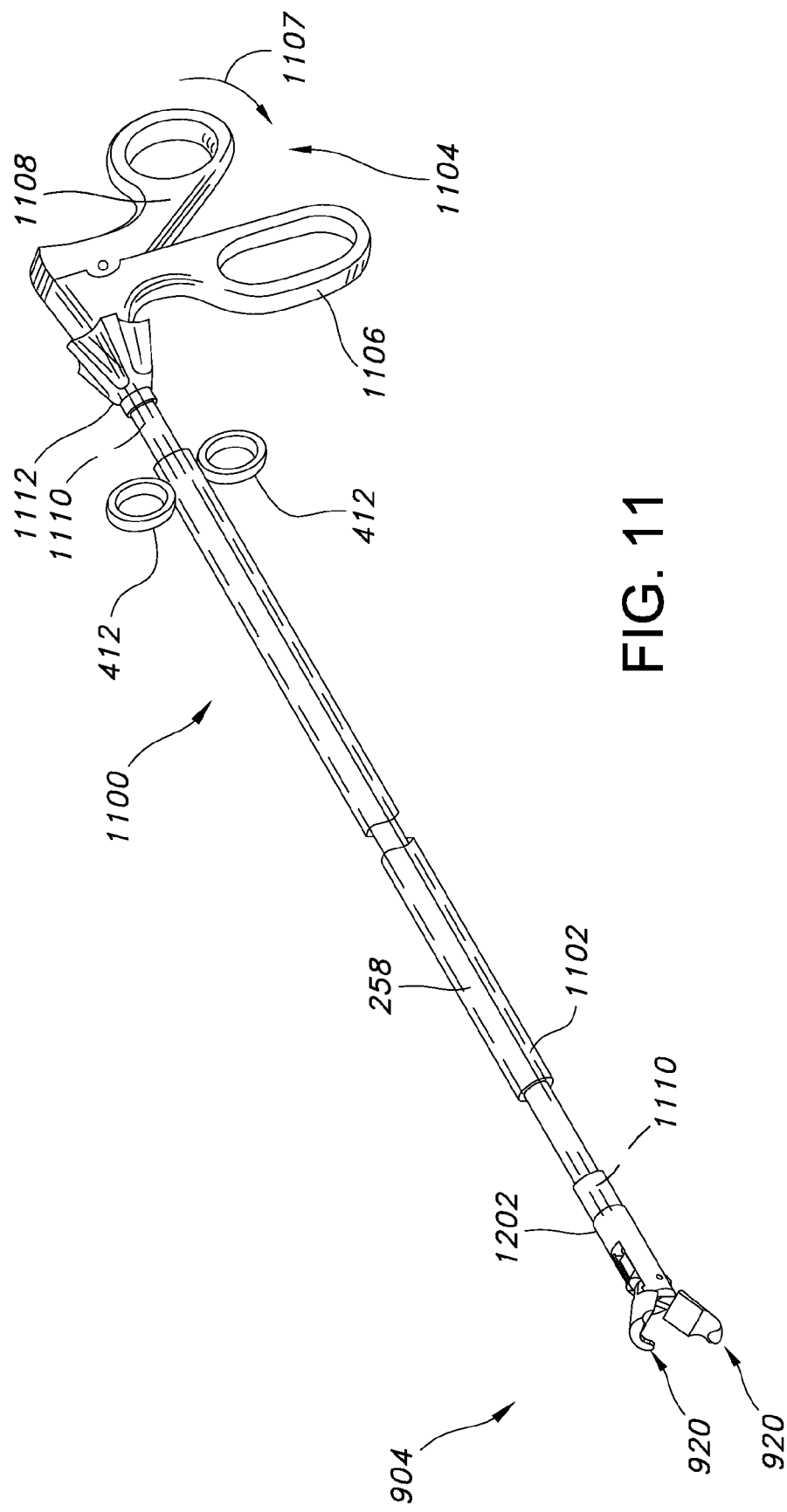
FIG. 11 illustrates one embodiment of a surgical instrument comprising the grasper device of FIG. 9, a shaft assembly and a hand piece.

The grasper device 904 illustrated in FIG. 9 utilizes a set of jaws 920 instead of the collets and collet lumens described above. The jaws 920 may be actuated by the clinician according to any suitable manner. For example, FIG. 11 illustrates an embodiment of a surgical instrument 1100 comprising the grasper device 904, a shaft assembly 1102 and a hand piece 1104. The hand piece 1104 may be configured to be grasped by the clinician and, in at least one embodiment, the hand piece 1104 may comprise a pistol grip including a stationary member 1106 and a movable member, or trigger 1108. In use the trigger 1108 may be moved toward the stationary member 1106 as indicated by arrow 1107, for example, in order to operate the grasper device 904 within a surgical site. In various embodiments, referring to FIG. 12, the jaw members 920 may be movably coupled to a housing, or clevis 1202 such that they may be moved, or pivoted, between open and closed positions about pivot pin 1204. In use, the jaw members 920 may be positioned in their closed, or at least partially closed, positions before they are inserted into a surgical site through a trocar or endoscope working channel 18, for example. Once positioned within the surgical site, the jaw members 920 may then be reopened. According to various embodiments, the shaft 1102 may be positioned within both the working channel 18 and the outer lumen 258, allowing the grasper device 904 to slide axially within the outer lumen 258, as described above.

Figure 12:
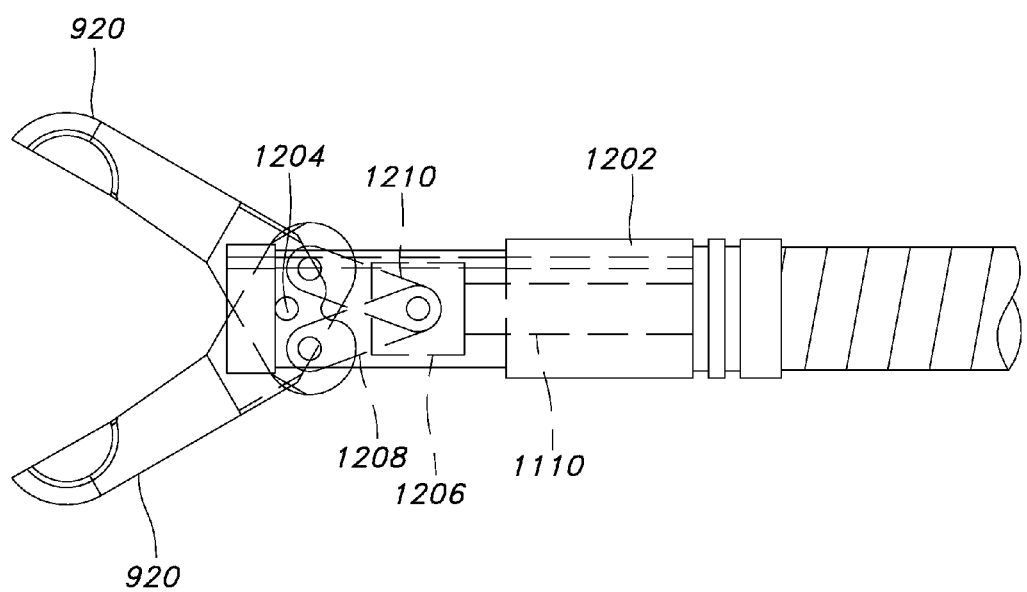
FIG. 12 illustrates one embodiment of a distal portion of the surgical instrument of FIG. 11.

In order to move the jaw members 920 between their open and closed positions, the trigger 1108 of the hand piece 1104 may be pivoted relative to the stationary member 1106 such that the trigger 1108 may displace an actuator, or rod 1110 relative to shaft 1102. In various embodiments, the actuator rod 1110 may be round, or any other suitable shape, and may be either solid or tubular. For example, the actuator rod 1110 may be hollow to allow suture to extend proximally therethrough. In either event, referring to FIG. 12, the actuator rod 1110 may be operably engaged with an actuator 1206 such that, when the trigger 1108 is pivoted toward the stationary member 1106 as described above, the actuator rod 1110 and the actuator 1206 may be slid proximally such that the actuator 1206 pulls on jaw links 1208 and 1210. When the jaw links 1208 and 1210 are pulled proximally, the jaw links 1208 and 1210 may apply a force to the jaws 920 such that they are pivoted about pivot pin 1204 into their closed state. In order to move jaws 920 into their open positions, the trigger 1108 may be moved away from the stationary member 1106 and, correspondingly, the actuator rod 1110 and the actuator 1206 may be moved distally by the trigger 1108. Similarly, the actuator 1206 may move links 1208 and 1210 distally such that the links 1208 and 1210 apply a force to jaws 920 and rotate them about pivot pin 1204 in the opposite, or open, direction. According to various embodiments, the instrument 1100 may also comprise a rotation knob 1112. The clinician may rotate the knob 1112 to cause the shaft 1102 and the grasper device 904 to rotate relative to the handle. FIG. 12 also illustrates the outer lumen 258 and loops 412 described above with respect to FIG. 4B. It will be appreciated that the outer lumen 258 may be used with the grasper device 904 in the same way that it is described above in use with the grasper device 204.

Various embodiments are described herein with a jaw-based grasper device 904 and a collet-based grasper device 204, 704. It will be appreciated, however, that any of the embodiments described herein may be implemented with any suitable style of grasper device including, for example, a collet-based or a jaw-based grasper device. For example, the needle 700 could alternately be used with a jaw-based grasper device, where the jaws may have grooves for receiving the collar 708 (e.g., similar to the grooves 756 in the collet fingers 752 of the collet 750). Also, for example, the needle 900 could alternately be used with a collet-based grasper device where the collet fingers define a cavity corresponding to the shape of the ball 908.

Figure 13:
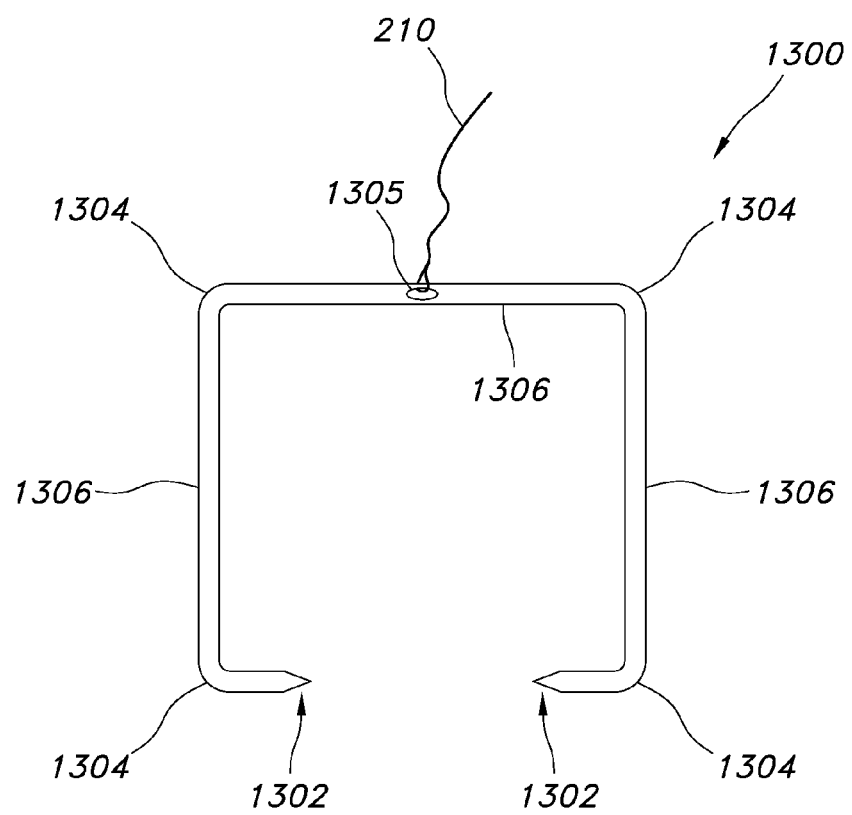
FIG. 13 illustrates one embodiment of a flexible jointed needle.

FIG. 13 illustrates one embodiment of a flexible jointed needle 1300. The needle 1300 may comprise straight sections 1306 connected by curved sections 1304. Although four curved sections 1304 and four straight sections 1306 are shown, it will be appreciated that any suitable number of curved and straight sections, and hence, any suitable polygonal shape may be used. In some example embodiments, the curved sections 1304 and the straight sections 1306 may be made from the same material (e.g., nitinal, or another resilient material as described above). Also, in other example embodiments, the curved sections 1304 may be made from a resilient material while the straight sections 1306 may be made from another material (e.g., a less expensive material). The needle 1300 may be capable of being substantially straightened, for example, by straightening the curved sections 1304. Accordingly, the needle 1300 may be used with any of the grasper assemblies 204, 704, 902 described above. Although the needle 1300 is pictured with two leading edges 1302, it will be appreciated, that a jointed needle may be provided with a leading edge 1302 and a back end (not shown) for example, similar to the needles 202, 700 and 900 described above.

In various embodiments, surgical instruments utilizing various embodiments of the needles 202, 700, 900, 1300 and/or grasper assemblies 204, 704, 904 may be employed in conjunction with a flexible endoscope, such as a GIF-100 model available from Olympus Corporation, for example. In at least one such embodiment, the endoscope, a laparoscope, or a thoracoscope, for example, may be introduced into the patient trans-anally through the colon, the abdomen via an incision or keyhole and a trocar, or trans-orally through the esophagus, for example. These devices may assist the clinician to guide and position the grasper assemblies and/or needles near the tissue treatment region to treat diseased tissue on organs such as the liver, for example. In another embodiment, these devices may be positioned to treat diseased tissue near the gastrointestinal (GI) tract, esophagus, and/or lung, for example. In various embodiments, the endoscope may comprise a flexible shaft where the distal end of the flexible shaft may comprise a light source, a viewing port, and at least one working channel. In at least one such embodiment, the viewing port may transmit an image within its field of view to an optical device such as a charge coupled device (CCD) camera within the endoscope, for example, so that an operator may view the image on a display monitor (not shown).

It will be appreciated that the terms "proximal" and "distal" are used herein with reference to a clinician manipulating an end of an instrument extending from the clinician to a surgical site (e.g., through a trocar, through a natural orifice, through an open surgical site, etc.). The term "proximal" refers to the portion closest to the clinician, and the term "distal" refers to the portion located away from the clinician. It will be further appreciated that for conciseness and clarity, spatial terms such as "vertical," "horizontal," "up," and "down" may be used herein with respect to the drawings. However, surgical instruments are used in many orientations and positions, and these terms are not intended to be limiting and absolute.

While several embodiments have been illustrated and described, and while several illustrative embodiments have been described in considerable detail, the embodiments are not intended to restrict or in any way limit the scope of the appended claims to such detail. Additional advantages and modifications may readily appear to those skilled in the art. Those of ordinary skill in the art will readily appreciate the different advantages provided by these various embodiments.

While several embodiments have been described, it should be apparent, however, that various modifications, alterations and adaptations to those embodiments may occur to persons skilled in the art with the attainment of some or all of the advantages of the embodiments. For example, according to various embodiments, a single component may be replaced by multiple components, and multiple components may be replaced by a single component, to perform a given function or functions. This application is therefore intended to cover all such modifications, alterations and adaptations without departing from the scope of the appended claims.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the embodiments described herein will be processed before surgery. First a new or used instrument is obtained and, if necessary, cleaned. The instrument may then be sterilized. In one sterilization technique, the instrument is placed in a closed and sealed container, such as a plastic or TYVEK® bag. The container and instrument are then placed in a field of radiation that may penetrate the container, such as gamma radiation, x-rays, or higher energy electrons. The radiation kills bacteria on the instrument and in the container. The sterilized instrument may then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The embodiments are not to be construed as limited to the particular embodiments disclosed. The embodiments are therefore to be regarded as illustrative rather than restrictive. Variations and changes may be made by others without departing from the scope of the claims. Accordingly, it is expressly intended that all such equivalents, variations and changes that fall within the scope of the claims be embraced thereby.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical applications to thereby enable one of ordinary skill in the art to utilize the various embodiments and with various modifications as are suited to the particular use contemplated. It is intended that the claims submitted herewith define the overall scope.

What is claimed is:

1. A surgical suturing device, comprising:
    a grasper device having a distal grasping end, the grasper device comprising:
        a collet comprising a plurality of fingers at the distal grasping end of the grasper device, wherein the plurality of fingers collectively define a concave feature wherein the concave feature comprises a groove; and
        a collet lumen, wherein the collet is positioned within the collet lumen, wherein the collet and collet lumen are translatable relative to one another from a first state where the plurality of fingers are in an open position to a second state where the plurality of fingers are in a closed position;
    an outer lumen coupled to a control mechanism for the surgical suturing device, wherein the grasper device is positioned within the outer lumen, and wherein the grasper device is translatable from a first position wherein the distal grasping end extends distally from the outer lumen to a second position where the distal grasping end is within the outer lumen; and
    a curved resilient suturing needle defining a leading end and a back end, wherein the back end defines a needle feature that is shaped to match the concave feature of the grasper device such that the back end of the needle is received by the grasper device and wherein the needle feature comprises a collar sized to be received by the groove.

2. The surgical device of claim 1, wherein the needle feature is rounded.

3. The surgical device of claim 1, wherein the needle is resilient from a substantially straight position to a curved resting position.

4. The surgical device of claim 1, wherein the outer lumen is configured to be translatable relative to a working channel of an endoscope.

5. The surgical device of claim 1, wherein the back end of the suturing needle is releaseably received into the collet of the grasper device.

* * * * *

UNITED STATES PATENT AND TRADEMARK OFFICE
CERTIFICATE OF CORRECTION

| | |
|---|---|
| PATENT NO. | : 8,480,689 B2 |
| APPLICATION NO. | : 12/202740 |
| DATED | : July 9, 2013 |
| INVENTOR(S) | : Spivey et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1010 days.

Signed and Sealed this
Thirtieth Day of December, 2014

Michelle K. Lee
*Deputy Director of the United States Patent and Trademark Office*